(12) United States Patent
Nielsen et al.

(10) Patent No.: US 10,006,073 B2
(45) Date of Patent: Jun. 26, 2018

(54) USE OF BACILLUS COMPOSITION FOR INCREASING THE AMOUNT OF AVAILABLE SUGARS IN ANIMAL FEED

(71) Applicant: Chr. Hansen A/S, Hørsholm, Denmark (DK)

(72) Inventors: Beatrice Nielsen, Hvidovre (DK); Tina Styrishave, Ringsted (DK); Mette Dines Cantor, Birkeroed (DK); Patrick Derkx, Tikoeb (DK); Jonna Nielsen, Hoersholm (DK); Robert Lantz, Hilliard, OH (US)

(73) Assignee: CHR, HANSEN A/S, Hoersholm (DK)

( * ) Notice: Subject to any disclaimer, the term of this patent is extended or adjusted under 35 U.S.C. 154(b) by 421 days.

(21) Appl. No.: 14/248,914

(22) Filed: Apr. 9, 2014

(65) Prior Publication Data

US 2014/0349331 A1 Nov. 27, 2014

(30) Foreign Application Priority Data

May 24, 2013 (EP) .................................. 13169189

(51) Int. Cl.
    C12Q 1/02       (2006.01)
    A23K 10/18      (2016.01)
    A23K 20/163     (2016.01)
    A23K 50/75      (2016.01)
    A23K 50/30      (2016.01)
    A23K 50/60      (2016.01)

(52) U.S. Cl.
    CPC ............... *C12Q 1/02* (2013.01); *A23K 10/18* (2016.05); *A23K 20/163* (2016.05); *A23K 50/30* (2016.05); *A23K 50/60* (2016.05); *A23K 50/75* (2016.05); *G01N 2333/32* (2013.01)

(58) Field of Classification Search
    None
    See application file for complete search history.

(56) References Cited

U.S. PATENT DOCUMENTS

| 2010/0062102 | A1* | 3/2010 | Knap | A23K 1/1826 426/2 |
| 2011/0262584 | A1* | 10/2011 | Knap | A23K 1/009 426/2 |
| 2012/0128827 | A1 | 5/2012 | Ochoa | |
| 2013/0064927 | A1 | 3/2013 | Davis et al. | |

FOREIGN PATENT DOCUMENTS

| CN | 101214004 A * | 7/2008 | ............... A23K 1/00 |
| EP | 2 011 858 A1 | 1/2009 | |
| WO | WO-03/093420 | 11/2003 | |
| WO | WO-2010/069990 | 6/2010 | |
| WO | WO-2010/110778 | 9/2010 | |
| WO | WO 2012110778 A2 * | 8/2012 | ............... A23K 1/009 |

OTHER PUBLICATIONS

Rodrigues, M.A. et al. 2011. Evaluation of Chlorella (Chlorophyta) as source of fermentable sugars via cell wall enzymatic hydrolysis. Enzyme Research 2011: 1-5. specif. pp. 1-3.*
Pettersson, D. et al. 1989. Enzyme supplementation of a poultry diet containing rye and wheat. British Journal of Nutrition 62: 139-149. specif. pp. 139,146,147.*
Kocher, A. et al. 2002. Effects of feed enzymes on nutritive value of soyabean meal fed to broilers. British Poultry Science 43: 54-63. specif. pp. 54, 55.*
Bedford, M.R. et al. 1998. Exogenous enzymes for pigs and poultry. Nutrition Research Reviews 11: 91-114. specif. pp. 91, 100, 103, 104.*
English translation. Qiu, Y. et al. 2008. Method for using rough material containing vegetable fibre to produce feed. Chinese Patent Application Publication No. CN101214004(A). specif. pp. 2, 3, 4, 6.*
Choct, M. 1997. Feed non-starch polysaccharides: chemical structures and nutritional significance. Feed Milling International, June issue, pp. 13-26. specif. pp. 2, 9.*
Navarro, D. et al. 2010. Automated assay for screening the enzymatic release of reducing sugars from micronized biomass. Microbial Cell Factories 9(58): 1-13. specif. pp. 1, 3, 4, 10, 13.*
Van Dyk, J.S., et al. 2010. Identification of endoglucanases, xylanases, pectinases and mannanases in the multi-enzyme complex of Bacillus licheniformis SVD1. Enzyme and Microbial Technology 47: 112-118. specif. p. 112, 116.*
Teng, D. et al. 2006. Cloning of B-1,3-1,4-glucanase gene from Bacillus licheniformis EGW039 (CGMCC 0635) and its expression in *Escherichia coli* BL21 (DE3). Applied Microbiology and Biotechnology 72: 705-712. specif. p. 705.*
Knap, I. et al. 2010. Bacillus licheniformis prevents necrotic enteritis in broiler chickens. Avian Diseases 54: 931-935. specif. pp. 931, 932.*

(Continued)

*Primary Examiner* — Renee Claytor
*Assistant Examiner* — Sharon M. Papciak
(74) *Attorney, Agent, or Firm* — Foley & Lardner LLP

(57) ABSTRACT

Methods are provided for assaying whether a *Bacillus* composition comprising at least one *Bacillus* strain is capable of increasing the amount of sugar available from animal feed comprising non-starch polysaccharides (NSP) in vivo when the *Bacillus* composition and animal feed are fed to an animal. Methods also are provided for increasing the amount of sugar available from animal feed comprising non-starch polysaccharides (NSP) when the animal feed is fed to an animal, comprising adding to the animal feed a *Bacillus* composition comprising at least one *Bacillus* strain, wherein the composition produces 120 hexose equivalents (μmol/ml) or more when measured by the method described herein. Animal feeds comprising 14% (w/w) or more of non-starch polysaccharides (NSP) if the animal feed is for a piglet, lactating sow, broiler or layer, or 19% (w/w) or more of non-starch polysaccharides (NSP) if the animal feed is for a grower-finisher pig or gestating sow, and a *Bacillus* composition comprising at least one *Bacillus* strain, as well as methods and uses relating thereto, also are provided.

18 Claims, 4 Drawing Sheets

(56) References Cited

OTHER PUBLICATIONS

Figure 1:
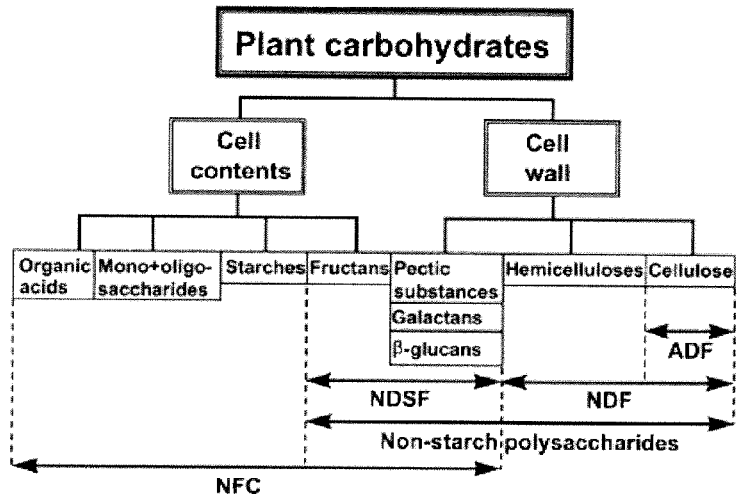

Full English translation of Qiu et al. Chinese Patent Application Publication No. CN 101214004 A; Publication Date: Jul. 9, 2008. pp. 1-11, specif. pp. 1, 3, 6, 7, 10.*

Tao et al. Comparative study on the digestion of different feed combinations by three strains of bacilli. Feed Research 7: 41-43.in CN.*

Hand/human English translation of Tao et al. Comparative study on the digestion of different feed combinations by three strains of bacilli. Feed Research 7: 41-43, renumbered as pp. 1-18. specif. pp. 3, 4, 6, 15.*

Barletta, "Introduction: Current Market and Expected Developments," Enzymes in Farm Animal Nutrition, 2nd ed., pp. 1-11, 2011.

Hall, M.B. "Challenges with nonfiber carbohydrate methods." J. Animal Sci. vol. 81, No. 12, pp. 3226-3232, 2003.

Knudsen, K.E.B. and Lærke, H.N.,"Chapter 8: Carbohydrate digestion and absorption," Nutritional physiology of pigs, Videnscenter for svineproduktion, 2013.

Woyengo et al., "Nutrient digestibility and performance responses of growing pigs fed phytase- and xylanase-supplemented wheat-based diets." J Anim Sci 2008, 86:848-857, 2008.

\* cited by examiner

USE OF *BACILLUS* COMPOSITION FOR INCREASING THE AMOUNT OF AVAILABLE SUGARS IN ANIMAL FEED

FIELD OF THE INVENTION

Enzyme activity for degrading non-starch polysaccharides (NSP) can be analyzed for each single enzyme (i.e. endo-cellulases) or by the measurement of the degradation products when NSP is degraded: reducing sugars. A number of *Bacillus* strains have been tested in a newly developed assay measuring reducing sugars after incubation in pig and poultry feed and have been found to be capable of increasing the amount of available sugar from animal feed comprising non-starch polysaccharides (NSP).

The invention relates to the use of a *Bacillus* composition comprising at least one *Bacillus* strain for increasing the amount of reducing sugars in animal feed comprising non-starch polysaccharides (NSP) and to the newly developed feed-based method for assaying the amount of reducing sugars in feed to which has been added a *Bacillus* composition. In particular embodiments, the invention relates to the use of a *Bacillus* composition comprising at least one *Bacillus* strain for increasing the amount of reducing sugars in animal feed comprising 14% (w/w) or more of non-starch polysaccharides (NSP) if the animal feed is for a piglet, lactating sow, broiler or layer or 19% (w/w) or more of non-starch polysaccharides (NSP) if the animal feed is for a grower-finisher pig or gestating sow.

BACKGROUND OF THE INVENTION

Increasing raw material prices worldwide are a challenge for animal production with poor economy. Furthermore, feed utilization is not optimal, as pigs and poultry do not produce NSP enzymes and therefore up to 15-25% of the feed ration is not digested (Barletta, 2011).

Animals use enzymes to digest feed. Enzymes can be produced by the animal itself or by the microbes present in the gut or they can be added as feed additives. 15-25% of the feed is not digested by pigs and poultry due to lack of enzymes or due to the content of indigestible anti-nutritional factors interfering with the digestive process (Barletta, 2011).

In feed rations comprising by-products such as Dried Distillers Grains with Solubles (DDGS) or wheat bran even a larger amount of nutrients from the feed will not be digested due to high amounts of non-starch polysaccharides (NSP) as pigs and poultry cannot produce NSP enzymes.

WO03/093420 describes methods for enzymatic hydrolysis of lignocellulose substrates for the production of ethanol and assays using sterilized and concentrated culture supernatants from unidentified strains.

WO03/093420 provides no suggestion or hint that a *Bacillus* strain can be used in a method for assaying whether a *Bacillus* composition comprising at least one *Bacillus* strain is capable of increasing the amount of available sugar from animal feed comprising non-starch polysaccharides (NSP), said method comprising incubating the animal feed with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

SUMMARY OF THE INVENTION

The problem to be solved by the present invention is to provide a means for increasing the content of non-starch polysaccharides (NSP) in animal feed without compromising animal performance.

The solution is adding a *Bacillus* composition comprising at least one *Bacillus* strain which is capable of increasing the amount of available sugar from animal feed comprising non-starch polysaccharides (NSP) and increasing the content of non-starch polysaccharides (NSP) in the animal feed. This solution is based upon a method for assaying developed by the present inventors for the identification of *Bacillus* strains having the property of increasing the amount of available sugar from animal feed comprising non-starch polysaccharides (NSP).

While it is known that certain *Bacillus* spp. have enzyme producing abilities including NSP-enzymes it has to the knowledge of the present inventors never been considered to add a *Bacillus* composition comprising at least one *Bacillus* strain which is capable of increasing the amount of available sugars in animal feed in order to increase the energy availability from animal feed comprising non-starch polysaccharides (NSP) and thus make it possible to add non-starch polysaccharides (NSP) to animal feed in a higher amount than if no such *Bacillus* composition is added.

Presently, animal feed comprises less than 14% (w/w) of non-starch polysaccharides (NSP) if the animal feed is for a piglet, lactating sow, broiler or layer or less than 19% (w/w) of non-starch polysaccharides (NSP) if the animal feed is for a grower-finisher pig or gestating sow.

The present invention provides a method for increasing the amount of available sugar from animal feed comprising 14% (w/w) or more of non-starch polysaccharides (NSP) if the animal feed is for a piglet, lactating sow, broiler or layer or 19% (w/w) or more of non-starch polysaccharides (NSP) if the animal feed is for a grower-finisher pig or gestating sow, said method comprising adding to the animal feed a *Bacillus* composition comprising at least one *Bacillus* strain, said *Bacillus* composition being capable of producing 120 hexose equivalents (μmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

LEGEND TO FIGURES

FIG. 1

Plant carbohydrate fractions. ADF=acid detergent fiber, β-glucans=(1→3)(1→4)-β-D-glucans, NDF=neutral detergent fiber, NDSF=neutral detergent-soluble fiber (includes all non-starch polysaccharides not present in NDF), NFC=non-NDF carbohydrates. (Hall, 2003)

FIG. 2

Standard curve showing reducing sugar (hexose) equivalents [μmol/ml]=$OD_{540}$*11.44 ($R^2$=0.95)

FIG. 3a

Reducing sugar units in feed to which has been added different *Bacillus* products (mean of 4 replicates) after inoculation. Control=no *Bacillus* added

FIG. 3b

Reducing sugar units in feed to which has been added different *Bacillus* strains (mean of 3 replicates) after inoculation. Control=no *Bacillus* added, A=*Bacillus subtilis*, B=*Bacillus amyloliquefaciens*, C=*Bacillus amyloliquefaciens*, *Bacillus amyloliquefaciens* DSM 27033, E=*Bacillus amyloliquefaciens*, *Bacillus amyloliquefaciens* DSM 28634, and G=*Bacillus subtilis*

FIG. 4

Reducing sugar in poultry feed samples to which 0.3% bile and three different *Bacillus* products have been added (mean of 3 replicates)

FIG. 5

Reducing sugar in swine feed samples to which 0.3% bile and three different *Bacillus* products have been added (mean of 3 replicates)

FIG. 6

Reducing sugar in feed samples to which amyloglucosidase and three different *Bacillus* strains have been added (A=*Bacillus amyloliquefaciens*, *Bacillus amyloliquefaciens* DSM 27033 and C=*Bacillus subtilis*) (mean of 3 replicates)

FIG. 7

Reducing sugar in feed samples to which amylase and pancreatin and two different *Bacillus* strains have been added (A=*Bacillus amyloliquefaciens* and *Bacillus amyloliquefaciens* DSM 27033) (mean of 3 replicates)

DETAILED DESCRIPTION OF THE INVENTION

The present inventors have developed a feed assay for determining the amount of reducing sugars in feed. The assay is based upon a method (DNS) which has been used for laboratory media, but which has not been previously been developed for use in a feed based assay.

The inventors surprisingly found using this feed based assay measuring reducing sugar that certain *Bacillus* species, in particular *Bacillus subtilis* strains such as *Bacillus subtilis* DSM 17231 and DSM 19489, have a high capability to degrade non-starch polysaccharides to reducing sugars that can be absorbed by monogastric animals as pigs and poultry.

Non-starch polysaccharides (NSP) in a diet are defined as the part of the crude carbohydrate fraction when sugar (mono- and oligosaccharides), organic acids and starch are taken away (FIG. 1).

Carbohydrates are classified according to the degree of polymerization (DP): mono- and disaccharides (DP=1-2), oligosaccharides (DP=3-9) and polysaccharides (DP≥10). Polysaccharides are further divided into two subgroups according to their digestibility: starch and non-starch polysaccharides (Knudsen, K. E. B. and Lærke, H. E. N., 2013). Consistent with the above, the term "non-starch polysaccharides (NSP)" in the present description and claims is defined as polysaccharides with a degree of polymerization≥10 excluding starch.

Non-starch polysaccharides consist of many different plant polymers, including i.e. β-glucans, cellulose, hemicellulose, and pectic substances. Non-starch polysaccharides can be determined by gas-liquid chromatography (component neutral sugars) and by colorimetry (uronic acids) (Woyengo et al (2008)).

Standard feed for pigs and poultry contains typically corn or cereals as barley and wheat as well as soy bean meal as energy and protein source respectively. As feed prices have increased many different by-products have been included in feed rations, i.e. Dried Distillers Grains with Solubles (DDGS) (a by-product from ethanol production), wheat bran (hard outer layer of wheat), wheat middlings (by-product from the wheat milling industry), soy hulls (by-product from the soybean oil and soybean meal industry). All these by-products have a high content of NSP in common but also standard feed components as corn, cereal and soy bean contain typically 10-15% NSP (Table 1).

TABLE 1

Examples of amount and content of NSP in various feed components

| Feed ingredient | Amount of NSP % (w/w) of dry matter | Examples of NSP content |
| --- | --- | --- |
| Cereals | 10-15 | Beta-glucans, hemicellulose (barley) |
| Corn | 10-15 | Hemicellulose + cellulose |
| Sorghum | 10-15 | |
| DDGS | 25-35 | Hemicellulose + cellulose |
| Wheat bran | 25-35 | |
| Soy bean meal | 20-35 | Pectins |

The present invention relates to all feed components comprising NSP and the above mentioned standard feed components and by-products should only be seen as non-limiting examples of feed components comprising NSP which are presently used or could be used in animal feed.

Enzyme activity for degrading non-starch polysaccharides (NSP) can be analyzed for each single enzyme (i.e. endo-cellulases and xylanases) or by the measurement of the degradation products when NSP is digested: reducing sugars. It is very demanding to test for all relevant enzymes—and maybe not even possible in practice as we may not know all relevant enzymes nor have methods for assaying for all of them. Accordingly, the present inventors developed a new assay which is simulating the in vivo situation measuring the amount of reducing sugars in feed incubated with *Bacillus* resulting from the combined effect of the various enzymes. The assay simulates the situation when feed is ingested by the animal and is digested in the digestive tract.

In accordance herewith the present invention provides a method for assaying whether a *Bacillus* composition comprising at least one *Bacillus* strain is capable of increasing the amount of available sugar from animal feed comprising non-starch polysaccharides (NSP), said method comprising incubating the animal feed with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

A reducing sugar is any sugar that either has a reactive aldehyde group or is capable of forming one to allow the sugar to act as a reducing agent. The reducing ends are formed by the enzymatic cleavage of the glycosidic bond between polymeric carbohydrates. Reducing sugars include glucose, glyceraldehyde and galactose as well as disaccharides, like lactose and maltose and can be measured by the Nelson-Somogyi (NS) or dintrosalicylic acid (DNS) method. DNS is an aromatic compound that reacts with reducing sugars and other reducing molecules to form 3-amino-5-nitrosalicylic acid, which absorbs light strongly at 540 nm.

Figure 3A:
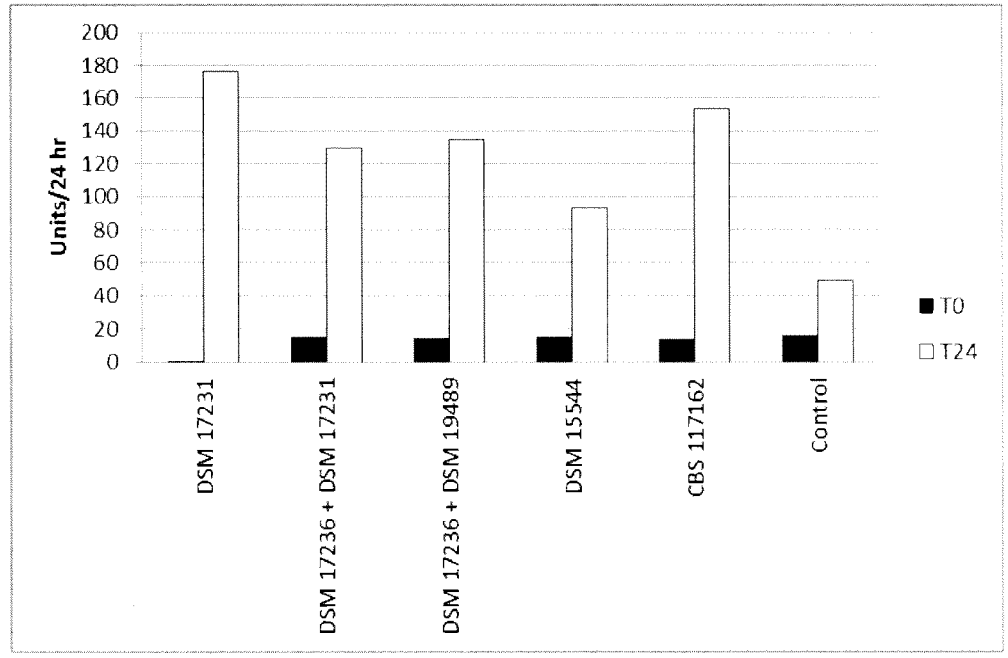
Figure 3B:
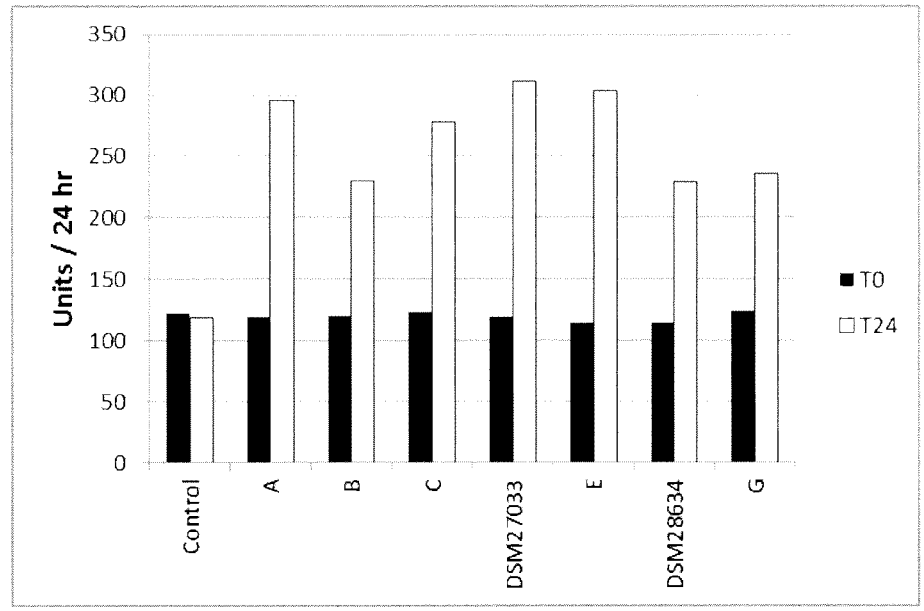

The ability of different *Bacillus* strains to degrade NSP to reducing sugars has been investigated in Example 2 and the results are provided in FIGS. 3a and 3b. The present findings show for the control in FIG. 3a 49 μmol/ml hexose equivalents when measured after 24 hours whereas all *Bacillus* compositions investigated demonstrate higher results. An activity of 90 hexose equivalents (μmol/ml) or more when measured after 24 hours was found for all presently investigated compositions. The compositions comprising *Bacillus*

*subtilis* DSM 17231 either alone or in combination with *Bacillus licheniformis* DSM 17236 or *Bacillus subtilis* DSM 19489 have an even higher activity of 120 hexose equivalents (µmol/ml) or more when measured after 24 hours. The highest activity is found for the *Bacillus* composition comprising *Bacillus subtilis* DSM 17231 or CBS 117162 only making *Bacillus* compositions consisting essentially of *Bacillus subtilis* a preferred embodiment, with *Bacillus* compositions consisting essentially of DSM 17231 being particularly preferred.

It is contemplated that other *Bacillus* compositions may exhibit similar good results if tested by the method of the present invention. To be within the scope of the present invention the *Bacillus* composition has to demonstrate an activity of 120 hexose equivalents (µmol/ml) or more when measured after 24 hours, most preferably 150 hexose equivalents (µmol/ml) or more when measured after 24 hours. Additional measurements have been made on a number of strains and the results of some of these have been provided in FIG. 3*b* from which it appears that also *B. amyloliquefaciens* strains provide good results.

The *Bacillus* composition to be used in the invention comprises at least one *Bacillus* strain, preferably one of the species *Bacillus amyloliquefaciens*, such as *Bacillus amyloliquefaciens* subsp. *amyloliquefaciens* or *Bacillus amyloliquefaciens* subsp. *plantarum, Bacillus* simplex, Bacillus licheniformis, Bacillus megaterium, Bacillus mojavensis, Bacillus pumilus, Bacillus safensis, Bacillus subtilis, Bacillus atrophaeus, Bacillus methylotrophicus, Bacillus siamensis, Bacillus vallismortis, B. coagulens, B. lentus, B. clausii, B. fusiformis or *Bacillus tequilensis.*

In a preferred embodiment the *Bacillus* composition comprises a *Bacillus subtilis* strain and/or a *Bacillus licheniformis* strain. Most preferably, the composition comprises at least one of the *Bacillus subtilis* strains with accession numbers DSM 17231 or DSM 19489, the *Bacillus licheniformis* strain with accession number DSM 17236, DSM 28634; or a mutant of any of these strains, or the *B. amyloliquefaciens* strain DSM 27033, or a mutant of this strain.

To be within the scope of the present invention the *Bacillus* composition comprising the *Bacillus subtilis* strain DSM 17231 or the *Bacillus subtilis* strain DSM 19489 or both, and/or the *Bacillus licheniformis* strain DSM 17236 or the *Bacillus licheniformis* strain DSM 28634 or both, and/or the *Bacillus amyloliquefaciens* strain DSM 27033, or a mutant of any of these strains, has to be capable of producing 120 hexose equivalents (µmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

A mutant strain of the *Bacillus subtilis* strains with accession numbers DSM 17231 or DSM 19489, or the *Bacillus licheniformis* strains with accession numbers DSM 17236 or DSM 28634 or the *Bacillus amyloliquefaciens* strain DSM 27033 can be obtained by subjecting the strain to mutagenization treatment as described in further detail below to obtain mutant strains and selecting for mutant strains having the desired properties. Alternatively, a selection is performed for spontaneously occurring mutants.

A bacterial "strain" as used herein refers to a bacterium which remains genetically unchanged when grown or multiplied. The multiplicity of identical bacteria is included.

"Wild type strain" refers to the non-mutated form of a bacterium, as found in nature.

A "mutant bacterium" or a "mutant strain" refers to a natural (spontaneous, naturally occurring) mutant bacterium or an induced mutant bacterium comprising one or more mutations in its genome (DNA) which are absent in the wild type DNA. An "induced mutant" is a bacterium where the mutation was induced by human treatment, such as treatment with any conventionally used mutagenization treatment including treatment with chemical mutagens, such as a chemical mutagen selected from (i) a mutagen that associates with or become incorporated into DNA such as a base analogue, e.g. 2-aminopurine or an interchelating agent such as ICR-191, (ii) a mutagen that reacts with the DNA including alkylating agents such as nitrosoguanidine or hydroxylamine, or ethane methyl sulphonate (EMS) or N-methyl-N'-nitro-N-nitroguanidine (NTG), UV- or gamma radiation etc. In contrast, a "spontaneous mutant" or "naturally occurring mutant" has not been mutagenized by man.

A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

Mutant bacteria as described above are non-GMO, i.e. not modified by recombinant DNA technology. As an alternative to above preferred method of providing the mutant by random mutagenesis, it is also possible to provide such a mutant by site-directed mutagenesis, e.g. by using appropriately designed PCR techniques or by using a transposable element which is integratable in bacterial replicons.

When the mutant is provided as a spontaneously occurring mutant the above wild-type strain is subjected to the selection step without any preceding mutagenization treatment.

Several species of *Bacillus* have GRAS status, i.e., they are generally recognized as safe. All *B. subtilis* strains are GRAS. The *Bacillus* strains described herein are aerobic and facultative spore formers. *Bacillus* species are the only spore formers that are considered GRAS. Feeding microorganisms that have GRAS status to livestock is an acceptable practice amongst producers, veterinarians, and others in the livestock industry.

The invention relates to a *Bacillus* composition comprising cells of at least one *Bacillus* strain. The composition may comprise cells of at least one, at least two, at least three, at least four or even more *Bacillus* strains. If the composition comprises more than one strain, each of the strains may be present as 5%, 10%, 20%, 25%, 33%, 40%, 50%, 60%, 66%, 75%, 80%, 90% or 95% of the *Bacillus* cells.

*Bacillus* cells exist as bacillus spore cells and bacillus vegetative cells. When reference is made herein to *Bacillus* compositions or *Bacillus* strains, these include both spore cells and vegetative cells. When present in animal feed, the *Bacillus* cell may be spores or vegetative cells. When used in the method and uses of the invention the *Bacillus* cells are functional vegetative *Bacillus* cells, which can divide to produce more vegetative cells.

The relevant *Bacillus* strains of the composition may be present in a commercially relevant form known to the skilled person. Accordingly, in an embodiment the *Bacillus* strains of the composition are present as dried (e.g. spray dried)

cells or as frozen cells. The composition may be provided in any suitable form such as in the form of a liquid, a slurry, a powder or a pellet.

In a preferred embodiment the *Bacillus* composition comprises from $10^5$ to $10^{12}$ CFU/g, more preferably from $10^6$ to $10^{12}$ CFU/g, and most preferably from $10^2$ to $10^{12}$ CFU/g.

The term "CFU/g" relates to the gram weight of the composition as such, including suitable relevant additives present in the composition. As known to the skilled person a commercially relevant bacterial composition generally also comprises other relevant additives such as e.g. one carrier/ingredient of the group belonging to whey, whey permeate, calcium carbonate/limestone and anti-caking agents such as aluminum silicates and kieselgur (diatomaceous earth). It does not include the weight of a suitable container used to package the *Bacillus* composition. An embodiment relates to a composition packaged into a suitable container.

Compositions to be used in the present invention may include a *Bacillus* strain and carriers that make these compositions suitable for feeding to animals as a feed additive or as an additive for drinking water. Alternatively, the *Bacillus* strain may be formulated with animal feed ingredients, including feed protein and/or feed carbohydrates. Such combinations may be in the form of pellets that are extruded through standard pelleting processes.

The *Bacillus* composition as described herein is to be used as an additive to animal feed. The invention also provides a method for producing an animal feed or premix comprising adding a *Bacillus* composition of the invention to an animal feed.

As used herein the term "premix" refers to a *Bacillus* strain added to a carrier to make a premix which is then added to the feed at a desired inclusion rate and fed to the animal.

Another aspect of the invention relates to a method for feeding an animal comprising administering an animal feed or premix according to the invention to an animal.

By supplementing a *Bacillus* composition that can degrade NSP to reducing sugars the nutritional value of feed ingredients can be improved. An increased digestibility of the NSP can work in two ways: 1) It increases the availability of other nutrients, vitamins and minerals that are fixated by the NSP. NSP absorb water and results in an increased viscous mass of feed particles in the intestine of the animal. In this mass nutrients are trapped and not available for the animal. Increasing the availability of nutrients for the animal also results in reduced nutrient loss to the environment. 2) It also increases the energy supply from the NSP itself.

The new findings make the use of *Bacillus* strains capable of increasing the amount of reducing sugars in feed comprising non-starch polysaccharides possible in new ways:

The Use of Feed Rations with High NSP Content.

In standard feed rations including by-products the amount of NSP is less than 14% (w/w) if the animal feed is for a piglet, lactating sow, broiler or layer and less than 19% (w/w) if the animal feed is for a grower-finisher. Higher amounts of NSP would reduce pig or poultry performance because NSP cannot be digested by pigs and poultry. With the new findings provided by the present inventors it is possible to increase the amount of by-products such as DDGS, wheat bran, wheat middlings or soy huls in the feed or to use other by-products without reducing pig or poultry performance.

The present invention provides use of a *Bacillus* composition comprising at least one *Bacillus* strain for increasing the amount of available sugar from animal feed comprising 14% (w/w) or more of non-starch polysaccharides (NSP) if the animal feed is for a piglet, lactating sow, broiler or layer or 19% (w/w) or more of non-starch polysaccharides (NSP) if the animal feed is for a grower-finisher pig or gestating sow, said *Bacillus* composition being capable of producing 120 hexose equivalents (μmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

The present invention further provides an animal feed comprising 14% (w/w) or more of non-starch polysaccharides (NSP) if the animal feed is for a piglet, lactating sow, broiler or layer or 19% (w/w) or more of non-starch polysaccharides (NSP) if the animal feed is for a grower-finisher pig or gestating sow, and a *Bacillus* composition comprising at least one *Bacillus* strain, said *Bacillus* composition being capable of producing 120 hexose equivalents (μmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

In a preferred embodiment, the animal feed according to the invention comprises at least one *Bacillus subtilis* strain such as the *Bacillus subtilis* strain DSM 17231 or the *Bacillus subtilis* strain DSM 19489 or both, or a mutant of any of these strains, which composition is capable of producing 120 hexose equivalents (μmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

In some embodiments the animal feed according to the invention comprises at least one *Bacillus licheniformis* strain such as the *Bacillus licheniformis* strain DSM 17236, or the *Bacillus licheniformis* strain DSM 28634 or both, or a mutant of any of these strains, which composition is capable of producing 120 hexose equivalents (μmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

In other embodiments the animal feed according to the invention comprises at least one *Bacillus amyloliquefaciens* strain such as the *Bacillus amyloliquefaciens* strain DSM 27033, or a mutant of this strain, which composition is capable of producing 120 hexose equivalents (μmol/ml) or more when measured by a method comprising incubating animal feed comprising 68% (w/w) ground corn, 20% (w/w) DDGS and 10% (w/w) Soy Bean Meal with the *Bacillus* composition at 37° C. for 24 hours, measuring the absorbance in a dinitrosalicylic acid (DNS) assay at $OD_{540}$ and calculating the amount of sugar (hexose) equivalents produced by correlating the measured absorbance to a standard curve.

The present invention provides uses, methods and animal feed comprising 19% NSP or more for grower finisher pigs and gestating sows such as 20% or more, 21% or more, 22% or more, 23% or more, 24% or more, 25% or more, 26% or more, 27% or more, 28% or more, 29% or more, 30% or moreof the feed ration measured as % (w/w) of dry matter (DM).

For piglets, lactating sows, broilers and layers the present invention provides uses, methods and animal feed comprising 14% NSP or more such as 15% or more, 16% or more, 17% or more, 18% or more, 19% or more, 20% or more of the feed ration measured as % (w/w) of dry matter (DM).

An example of a typical feed ration for grower finisher pigs could be 70% corn, 20% DDGS and 10% soy bean meal corresponding to approximately 17% NSP. Based upon the findings provided herein the amount of DDGS could be increased to 25% or 30% increasing the NSP content to 19% and 20% respectively (cf. Table 1). Also an increase to even 40% DDGS would be possible with the new invention increasing the NSP content to approx. 23% without having impact on pig performance. The NSP content in feed ingredients such as DDGS can vary a lot depending on growing conditions based on i.e. geography, temperature, humidity and harvest time. The calculations above should therefore only be seen as examples. Also feed rations vary a lot depending of feed company, availability and feed prices and also which animal species and segment the feed is applied to. For example will feed rations to piglets contain lower amounts of NSP compared to feed rations to grower finisher pigs. Piglets need a lot of energy and the intestine of the piglet is not fully developed so high NSP rations would have high impact on piglet performance. Based upon the finding provided herein it will however be possible to include some NSP containing by-products to piglets i.e. 5% or 10% or even 15% DDGS corresponding to approx. NSP content in the diet of 14%, 16% and 18%.

Reducing Energy in the Feed Ration Due to Improved Energy Availability

The *Bacillus* composition improve digestion of non-starch polysaccharides and releases energy that without the *Bacillus* composition was not available to the animal in that the amount of available sugar is increased by liberating the sugars present in the non-starch polysaccharides. Pigs and poultry are normally fed according to specific requirements of energy. With the *Bacillus* composition added energy in the feed can be reduced without reducing requirements needed by the animal. Energy is included as starch, protein and fat from i.e. corn, cereal and soybean. All these feed materials are representing about 70% of total production cost and a reduction in feed cost improves the economy for the farmer.

Improving Animal Growth—Opens New Markets (i.e. Grower Finisher Market)

Improved energy release from the feed results in improved growth of the animal. Pigs and poultry (e.g. broilers and turkey) are often slaughtered at a given weight and an improved growth will reduce the time it takes to slaughtering. Improved growth thus result in more animals slaughtered in a given time period.

Improved Manure Handling

Most diets containing high-NSP ingredients have poorer flowability than standard diets like corn-soybean meal diets. Depending on the design and dimensions of the bin, this may result in difficulties in getting the manure out of the bin.

The scope of the invention also includes uses, methods and products according to the invention for increasing the flowability of the manure.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Deposited Strains

The *Bacillus subtilis* strain has been deposited at DSMZ (Deutsche Sammlung von Mikroorganismen und Zellkulturen GmbH, Inhoffenstrasse 7B, D-38124 Braunschweig) under the accession number DSM 17231 with a deposit date of Apr. 7, 2005 by Chr. Hansen A/S, Denmark. The deposit has been made under the conditions of the Budapest Treaty on the International Recognition of the Deposit of Microorganisms for the Purposes of Patent Procedure.

The *Bacillus licheniformis* strain has been deposited at DSMZ (Deutsche Sammlung von Mikroorganismen und Zellkulturen GmbH, Inhoffenstrasse 7B, D-38124 Braunschweig) under the accession number DSM 17236 with a deposit date of Apr. 7, 2005 by Chr. Hansen A/S, Denmark. The deposit has been made under the conditions of the Budapest Treaty on the International Recognition of the Deposit of Microorganisms for the Purposes of Patent Procedure.

A further *Bacillus subtilis* strain has been deposited at DSMZ (Deutsche Sammlung von Mikroorganismen und Zelikulturen GmbH, Inhoffenstrasse 7B, D-38124 Braunschweig) under the accession number DSM 19489 with a deposit date of Jun. 27, 2007 by Chr. Hansen A/S, Denmark. The deposit has been made under the conditions of the Budapest Treaty on the International Recognition of the Deposit of Microorganisms for the Purposes of Patent Procedure.

A *Bacillus amyloliquefaciens* strain has been deposited at DSMZ (Deutsche Sammlung von Mikroorganismen und Zellkulturen GmbH, Inhoffenstrasse 7B, D-38124 Braunschweig) under the accession number DSM 27033 with a deposit date of Mar. 21, 2013 by Chr. Hansen A/S, Denmark. The deposit has been made under the conditions of the Budapest Treaty on the International Recognition of the Deposit of Microorganisms for the Purposes of Patent Procedure.

A further *Bacillus licheniformis* strain has been deposited at DSMZ (Deutsche Sammlung von Mikroorganismen und Zellkulturen GmbH, Inhoffenstrasse 7B, D-38124 Braunschweig) under the accession number DSM 28634 with a deposit date of Apr. 1, 2014 by Chr. Hansen A/S, Denmark. The deposit has been made under the conditions of the Budapest Treaty on the International Recognition of the Deposit of Microorganisms for the Purposes of Patent Procedure.

For all of the above-identified deposited microorganisms, the following additional indications apply:

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn Embodiments of the present invention are described below, by way of non-limiting examples.

EXAMPLES

Example 1

In Vitro Enzyme Test for Xylanase and Cellulase

Method for Cellulase Assay

*Bacillus* strains were grown in carboxymethyl cellulose (CMC) medium (per l: 10.0 g carboxymethyl cellulose (C9481, Sigma), 2.0 g Bacto Tryptone (cat. 211705, Becton Dickinson A/S, Denmark), 4 g $KH_2PO_4$, 4.0 g $Na_2HPO_4$, 0.2 g $MgSO_4.7H_2O$, 0.001 g $CaCl_2 2H_2O$, 0.004 g $FeSO_4.7H_2O$, pH 7) at 37° C. and vigorous magnetic agitation for 24 hours. Cellulase production was determined using the EnzChek Cellulase Substrat kit (cat. E33953, Life Technologies) according to the manufacturer's instructions. Shortly, culture supernatants were collected by centrifugation and distributed in MTPs (200 µl per well) in serial dilutions. Standard curves were constructed using cellulase from *Aspergillus niger* (C1184) starting from 2 U $ml^{-1}$ EnzChek substrate solution was added to the culture supernatants in Nunc 96 well Black FluoroNunc plates (cat. 237105, Thermo Fisher Scientific, NUNC Inc.). Fluorescence was recorded at excitation 360 nm/emission 420 nm after 30 min incubation (Enspire 2300 Multilabel Reader, Perkin Elmer Inc.). Cellulase activity was calculated from standard curves in two independent experiments and expressed as means (U $ml^{-1}$).

Method for Xylanase Assay

*Bacillus* cultures were grown in medium containing beech wood xylan (per l: 5.0 g xylan (X4252, Sigma), 2.0 g Yeast Extract (cat. 288620, Becton Dickinson A/S, Denmark), 5.0 g Bacto Peptone (cat. 211677, Becton Dickinson A/S, Denmark), 0.5 g NaCl, 0.5 g $MgSO_4.7H_2O$, 0.15 g $CaCl_2.2H_2O$, pH 7.5) at 37° C. and vigorous magnetic agitation for 24 hours. The xylanase assay was performed with the use of the EnzChek Ultra Xylanase Assay Kit (cat. E33650, Life Technologies) according to the manufacturer's instructions. Briefly, culture supernatants were collected by centrifugation, distributed in MTPs (200 µl per well), in serial dilutions and added xylanase substrate working solution. Fluorescence in culture supernatants was measured at excitation 360 nm/emission 420 nm after incubation for 30 min (Enspire 2300 Multilabel Reader, Perkin Elmer Inc.). *Thermomyces lanuginosis* (X2753) was used as standard enzyme and loaded in MTPs in serial dilutions, starting from 25 mU ml-1. Xylanase activity of the *Bacillus* strains was calculated from the standard curves and expressed as means (mU ml-1) of two independent assays.

Results and Conclusion

The results obtained in the in vitro assays are presented in Table 2.

TABLE 2

Cellulase and xylanase activity by Bacilli strains measured in vitro, mU/ml related to optical density (OD) mean of 2-4 analyses ± STD

| Bacilli strain/product | Cellulase | Xylanase |
|---|---|---|
| *B. licheniformis* DSM 17236 | 1673 ± 259 | 2.3 ± 0.4 |
| *B. subtilis* DSM 17231 | 4355 ± 1738 | 31.9 ± 27.3 |
| *B. subtilis* DSM 19489 | 276 ± 96 | 3.7 ± 2.6 |
| DSM 17231 + DSM 17236 (50:50) | 4436 ± 1344 | 2.3 ± 0.5 |
| *B. cereus* var. *toyoi* NCIMB 40112 (Toyocerin) | 95 ± 12 | 1.9 ± 0.4 |
| *B. subtilis* PB6, ATCC PTA-6737 (Clostat, Kemin) | 2560 ± 174 | Nt |
| *B. subtilis* C3102, DSM 15544 (Calsporin, Calpis) | 3300 ± 312 | Nt | nt = not tested

The results show that the *B. subtilis* strains have the highest cellulase and xylanase activity. The *B. cereus* strain was very low in both cellulose and xylanase production and was therefore not included in Example 2.

Example 2

Measurement of Amount of Reducing Sugars in Feed Incubated with a *Bacillus* Composition Materials and Methods The objective of this experiment was to examine the ability of different *Bacillus* strains to degrade NSP in pig feed and increase the available sugar amount. Grower-Finisher compound feed based on corn-soybean (Table 3) was autoclaved at 121° C. for 15 min for sterilization. Then the feed sample was diluted with sodium phosphate buffer to ensure a pH at about 6-6.5 throughout the whole experiment. *Bacillus* products (FIG. 3a) were added at a normal dosage rate suggested for finisher pigs. Strains (FIG. 3b) were obtained by inoculation with 2% overnight culture of the *Bacillus* strains, grown in Veal Infusion Broth (VIB) (Difco, 234420). A sample was taken for analysis for reducing sugar (DNS) (T=0). After incubation at 37° C. for 24 hours a sample was taken for cfu determination. Another sample was centrifuged and the supernatant used for determining DNS.

TABLE 3

Composition of compound feed used in the assay

| Ingredient | % of feed ration |
|---|---|
| Ground Corn | 68 |
| DDGS | 20 |
| Soy Bean Meal | 10.15 |
| Limestone | 1.09 |
| Salt | 0.43 |
| Lysine | 0.23 |
| Vitamins | 0.09 |

Reducing sugar was analyzed by 3.5-dinitrosalicylic acid (DNS) assay as follows:

Na-acetate buffer (100 mM, pH 6) was mixed with sterile filtered *Bacillus* sample supernatant and incubated at 40° C. for 10 min. DNS reagent was added to the test tube, mixed and incubated in a boiling water bath for 5 min. After cooling, absorbance was measured at 540 nm in a spectrophotometer.

Figure 2:
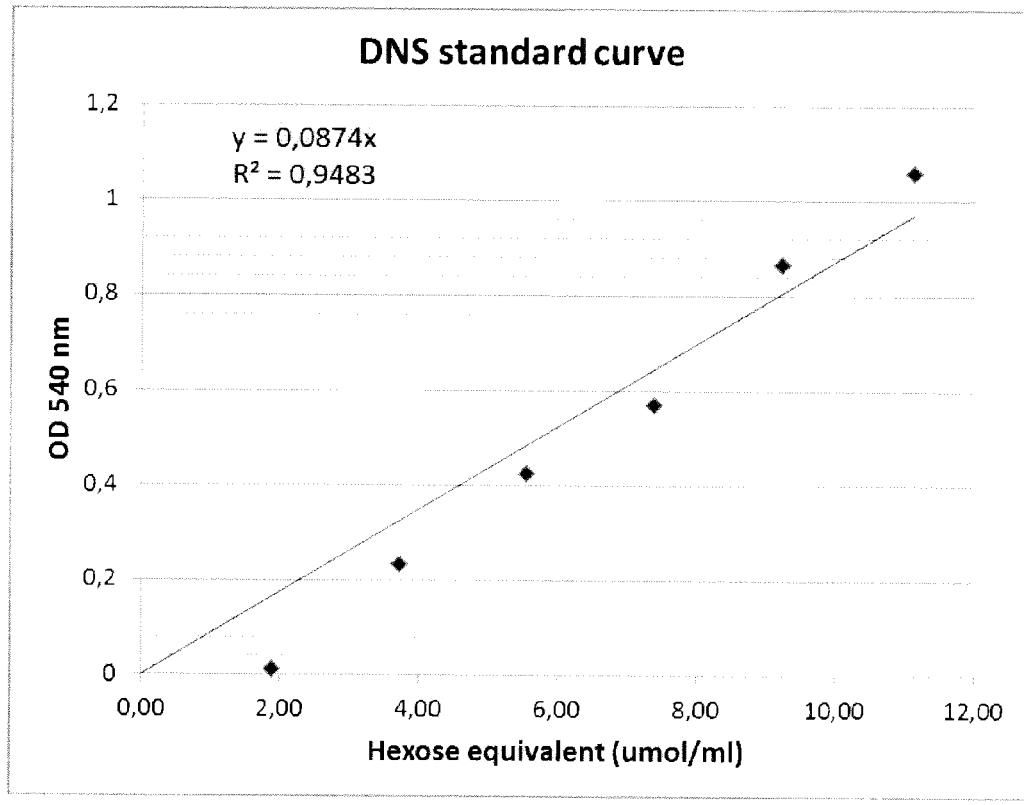

A standard curve was established with a glucose stock solution for presenting results in reducing sugar or enzyme units (amount of enzyme needed to release 1 μmol reducing hexose equivalent in 1 ml per time unit). (FIG. 2).

TABLE 4

Cell forming units (cfu/g) after 24 hours

| Bacillus strain | CFU at T24 (24 hours) |
|---|---|
| B. subtilis DSM 17231 | 1.3E+0.9 |
| B. licheniformis DSM 17236 + B. subtilis DSM 17231 (50/50) | 1.5E+09 |
| B. licheniformis DSM 17236 + B. subtilis DSM 19489 (50/50) | 4.0E+08 |
| B. subtilis C3102, DSM 15544 (Calsporin, Calpis) | 1.5E+09 |
| B. subtilis CBS 117162 (Animavit) | 1.3E+09 |

Results and Conclusion

All *Bacillus* products supply more nutrients to the animal by delivering more reducing sugars (FIG. 3a). The *B. subtilis* DSM 17231 products deliver 3 times or more reducing sugars than the control whereas the *B. subtilis* C3102 (DSM 15544) delivers less than 2 times more reducing sugars than the control. It is noteworthy that the combination of *B. licheniformis* DSM 17236 and *B. subtilis* DSM 19489 demonstrate good results in the present assay in spite of the modest results of the enzyme tests of the individual strains provided in Table 2 highlighting the importance of testing under realistic conditions using feed as a substrate.

FIG. 3b provides the results of 7 selected *Bacillus* strains and shows that both many *B. amyloliquefaciens* and *B. subtilis* strains demonstrate excellent effects compared to control.

Example 3

Simulate Intestinal Conditions with Bile Challenge

Bile Challenge

The objective of this experiment was to examine the ability of different *Bacillus* strains to degrade NSP in poultry feed and pig compound feed and increase the available sugar amount when simulating the GIT by adding bile. Vegetative cells of *B. subtilis* are very sensitive to small intestinal conditions. It has been shown that *Bacillus subtilis* had low survival at a level of 0.0002-0.002% after 1-3 hours with 0.2% bile salts Both poultry feed and pig compound feed based on corn-soybean (Table 3) was autoclaved at 121° C. for 15 min for sterilization. Then the feed sample was diluted with sodium phosphate buffer to ensure a pH at about 6-6.5 throughout the whole experiment. Bile salts (Bile extract porcine (Sigma-Aldrich B8631) were added at a concentration of 0.3%. *Bacillus* products were added at a normal dosage rate suggested for finisher pigs and poultry respectively. A sample was taken for analysis for reducing sugar (DNS) (T=0). After incubation at 37° C. for 24 hours a sample was taken, centrifuged and the supernatant used for determining DNS as outlined in Example 2.

Results and Conclusion

Figure 4:
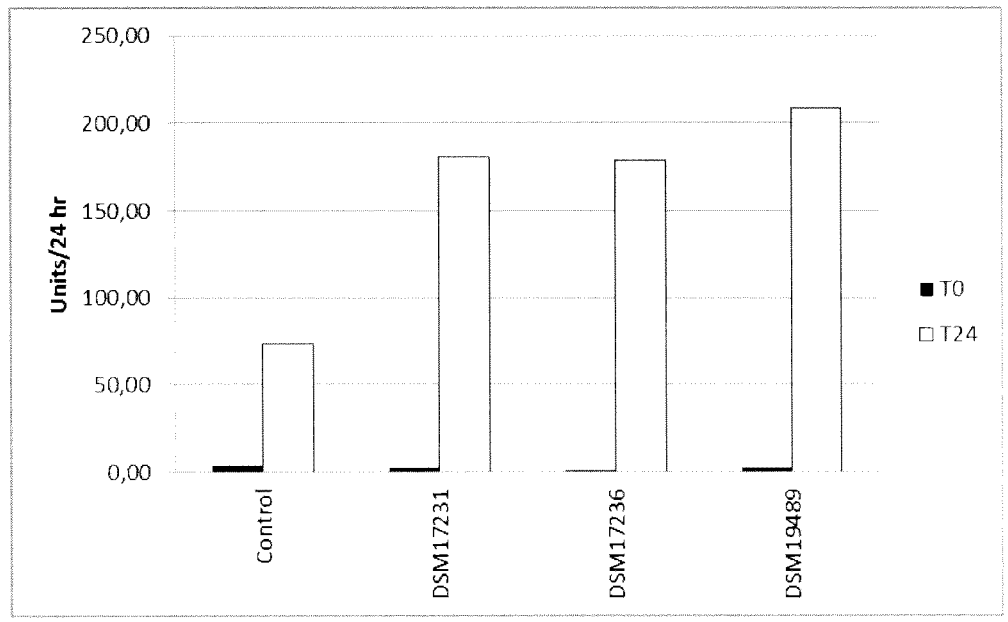

Most strains grow up to expected level above 1E+10 except DSM15544 that showed low growth below 1E+07 (data not shown). All *Bacillus* products supply more nutrients to the animal by delivering more reducing sugars compared to the control feed (FIG. 4).

In poultry feed the *B. subtilis* products deliver 2.5 times or more reducing sugars than the control even when the assay simulates the GIT with bile.

Figure 5:
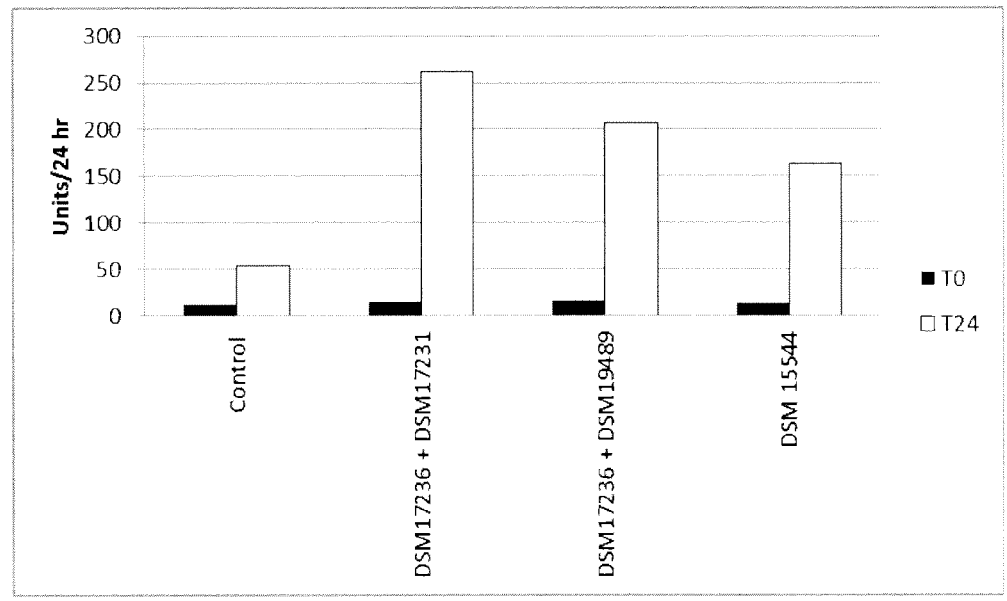

In swine feed bile both combination products surprisingly deliver 4-5 times reducing sugars than the control whereas the *B. subtilis* C3102 (DSM 15544) delivers 3 times more reducing sugars than the control (FIG. 5).

Example 4

Simulate Intestinal Conditions with Amylase Challenge

Amylase Challenge

The objective of this experiment was to examine the ability of different *Bacillus* strains to degrade NSP in pig feed and increase the available sugar amount when simulating the GIT by adding amylase. Pig compound feed based on corn-soybean (Table 3) was autoclaved at 121° C. for 15 min for sterilization. Then the feed sample was diluted with sodium phosphate buffer to ensure a pH at about 6-6.5 throughout the whole experiment. Feed assays were inoculated with 2% overnight culture of the *Bacillus* strains, grown in VIB media. A sample was taken for analysis for reducing sugar (DNS) (T=0). Amylase (gamma-amylase/amyloglucosidase (Sigma A7095)) was added at a concentration of 13 IU/ml assay. 3 replicates are tested. After incubation at 37° C. for 24 hours a sample was taken, centrifuged and the supernatant used for determining DNS as outlined in Example 2.

Amylase+Pancreatin Challenge

The same method was used as described above. Pancreatin (Sigma P7545), a product containing an enzyme mix produced by exocrine cells in the porcine pancreas including amylase, trypsin and lipase, was added at a concentration of 10 mg/ml together with amylase.

Results and Conclusion

Figure 6:
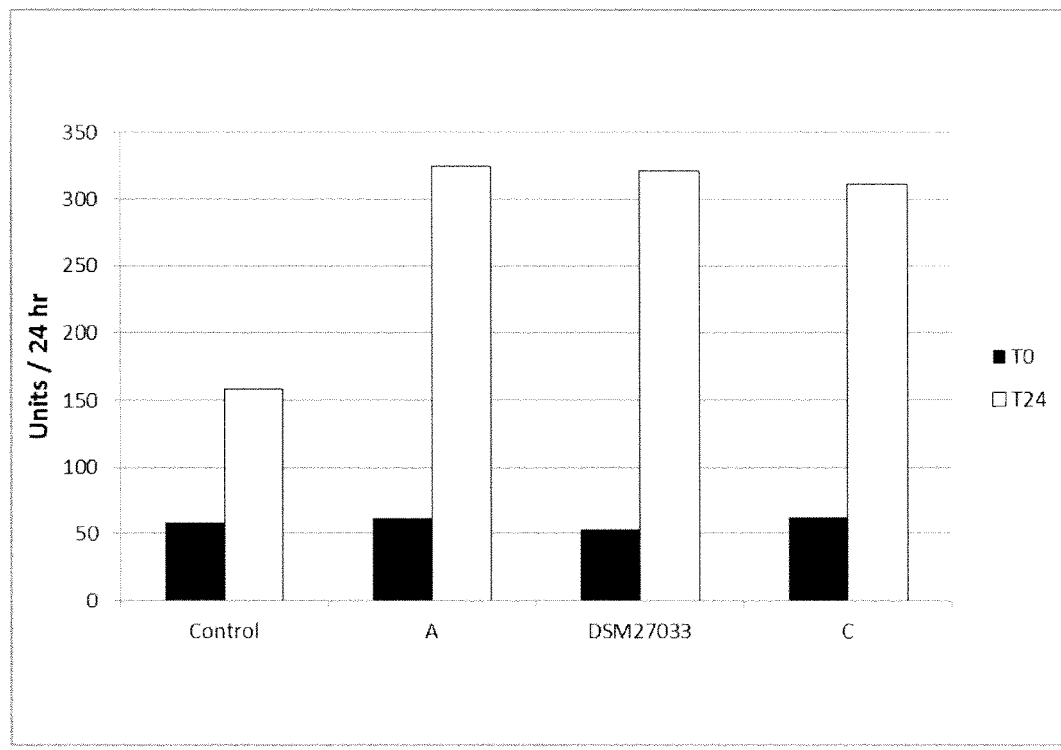
Figure 7:
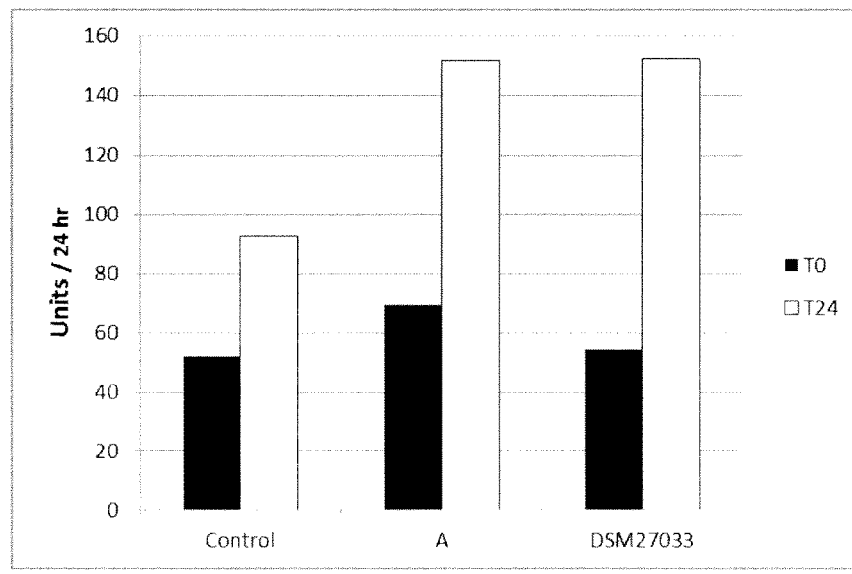

All three *Bacillus* products supply more nutrients to the animal by delivering more reducing sugars compared to the control feed (FIG. 6) and also when challenged by pancreatin (FIG. 7). The control figures are quite high, probably due to the addition of amylase.

REFERENCES

Barletta, 2011. Introduction: Current Market and Expected Developments. In "Enzymes in Farm Animal Nutrition", CABI, UK, 2nd ed. 1-11.
Hall, M. B. 2003. Challenges with nonfiber carbohydrate methods. J. Animal Sci. 81, 12, 3226-3232.
Knudsen, K. E. B. and Lærke, H. N., "Chapter 8: Carbohydrate digestion and absorption," in *Nutritional physiology of pigs*, Videnscenter for svineproduktion, 2013
Woyengo, T. A., Sands, J. S., Guenter W., and Nyachoti. C. M., 2008. Nutrient digestibility and performance responses of growing pigs fed phytase- and xylanase-supplemented wheat-based diets. J ANIM SCI 2008, 86:848-857.

The invention claimed is:
1. A method for increasing the amount of sugar available from an animal feed comprising non-starch polysaccharides (NSP) when the animal feed is fed to an animal, comprising:
adding to animal feed that comprises NSP, a *Bacillus* composition determined to produce 120 hexose equivalents (μmol/ml) or more when assayed by the method comprising incubating a *Bacillus* composition that comprises at least one *Bacillus* strain with animal feed that comprises NSP at 37°C. and a pH of about 6-6.5 for 24 hours to simulate in vivo conditions, measuring the absorbance in a dinitrosalicylic acid (DNS) assay at $OD_{540}$, and calculating the amount of hexose equivalents produced by correlating the measured absorbance to a standard curve.

2. The method of claim 1, wherein the animal feed is for a piglet, lactating sow, broiler or layer and comprises 14% (w/w) or more of non-starch polysaccharides (NSP), or is for a grower-finisher pig or gestating sow and comprises 19% (w/w) or more of non-starch polysaccharides (NSP).

3. The method according to claim 1, wherein the method increases the energy supply from non-starch polysaccharides in the animal feed when the animal feed comprising the added *Bacillus* composition is fed to an animal.

4. The method according to claim 1, wherein the method increases the nutritional value of the animal feed when the animal feed comprising the added *Bacillus* composition is fed to an animal by increasing the availability for the animal of nutrients, vitamins and minerals fixated by non-starch polysaccharides in the animal feed.

5. The method according to claim 1, wherein the method increases flowability of manure resulting from feeding the animal feed to an animal.

6. The method according to claim 1, wherein the *Bacillus* composition comprises at least one *Bacillus subtilis* strain.

7. The method according to claim 6 wherein the *Bacillus* composition comprises the *Bacillus subtilis* strain DSM 17231.

8. The method according to claim 6 wherein the *Bacillus* composition comprises the *Bacillus subtilis* strain DSM 19489.

9. The method according to claim 1, wherein the *Bacillus* composition comprises at least one *Bacillus licheniformis* strain.

10. The method according to claim 9, wherein the *Bacillus* composition comprises the *Bacillus licheniformis* strain DSM 17236.

11. The method according to claim 9, wherein the *Bacillus* composition comprises the *Bacillus licheniformis* strain DSM 28634.

12. The method according to claim 1, wherein the *Bacillus* composition comprises at least one *Bacillus amyloliquefaciens* strain.

13. The method according to claim 12, wherein the *Bacillus* composition comprises the *Bacillus amyloliqufaciens* strain DSM 27033.

14. The method according to claim 1, wherein the *Bacillus* composition comprises from $10^5$ to $10^{12}$ CFU/g of the at least one *Bacillus* strain.

15. The method according to claim 1, wherein the *Bacillus* composition comprises from $10^6$ to $10^{12}$ CFU/g of the at least one *Bacillus* strain.

16. A method for increasing the amount of sugar available from an animal feed comprising non-starch polysaccharides (NSP) when the animal feed is fed to an animal, comprising:

feeding to an animal a composition comprising animal feed that comprises NSP and a *Bacillus* composition determined to produce 120 hexose equivalents (μmol/ml) or more when assayed by the method comprising incubating a *Bacillus* composition that comprises at least one *Bacillus* strain with animal feed that comprises NSP at 37°C. and a pH of about 6-6.5 for 24 hours to simulate in vivo conditions, measuring the absorbance in a dinitrosalicylic acid (DNS) assay at $OD_{540}$, and calculating the amount of hexose equivalents produced by correlating the measured absorbance to a standard curve.

17. The method of claim 16, wherein the animal is a piglet, lactating sow, broiler or layer and the animal feed comprises 14% (w/w) or more of non-starch polysaccharides (NSP), or the animal is a grower-finisher pig or gestating sow and the animal feed comprises 19% (w/w) or more of non-starch polysaccharides (NSP).

18. The method of claim 16, wherein the composition comprises the *Bacillus* composition in an amount that provides from $10^5$ to $10^{12}$ CFU/g of the at least one *Bacillus* strain.

* * * * *